US006329186B1

(12) United States Patent
Nielsen et al.

(10) Patent No.: US 6,329,186 B1
(45) Date of Patent: Dec. 11, 2001

(54) GLUCOAMYLASES WITH N-TERMINAL EXTENSIONS

(75) Inventors: Rønfeldt Bjarne Nielsen, Virum; Allan Svendsen, Birkerød; Kirsten Bojsen, Hellerup; Jesper Vind, Lyngby; Henrik Pedersen, Bagsvœrd, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/455,679

(22) Filed: Dec. 7, 1999

Related U.S. Application Data

(60) Provisional application No. 60/111,674, filed on Dec. 10, 1998, and provisional application No. 60/126,740, filed on Mar. 29, 1999.

(30) Foreign Application Priority Data

Dec. 7, 1998 (DK) .............................................. 1998 01616
Mar. 24, 1999 (DK) .............................................. 1999 00409

(51) Int. Cl.$^7$ .............................. C12N 9/00; C12N 9/24; C12N 9/34
(52) U.S. Cl. ........................... 435/205; 435/183; 435/200

(58) Field of Search .................................. 435/69.1, 69.7, 435/183, 96, 203, 252.3, 205

(56) References Cited

FOREIGN PATENT DOCUMENTS

| 44 25 058 A1 | 1/1996 | (DE) . |
| 0 828 002 A2 | 3/1999 | (EP) . |
| WO 84/02921 | 8/1984 | (WO) . |
| WO 97/04078 | 2/1997 | (WO) . |

OTHER PUBLICATIONS

Joutsjoki et al. Secretion of the H.resinae glucoamylase P enzyme from T.reesei directed by the natural and cbh1 gene secretion signal. FEMS Microbiol. Letts. 1993, vol. 112:281–286, 1993.*

* cited by examiner

*Primary Examiner*—Rebecca E. Prouty
*Assistant Examiner*—Manjunath N. Rao
(74) *Attorney, Agent, or Firm*—Elias T. Lambiris; Jason I. Garbell

(57) ABSTRACT

The invention relates to a variant of a parent fungal glucoamylase, which exhibits improved thermal stability.

28 Claims, No Drawings

SEQUENCE LISTING

<160> NUMBER OF SEQ ID NOS: 45

<210> SEQ ID NO 1
<211> LENGTH: 534
<212> TYPE: PRT
<213> ORGANISM: Aspergillus niger
<220> FEATURE:
<221> NAME/KEY: SIGNAL
<222> LOCATION: (1)...(24)

<400> SEQUENCE: 1

```
Met Ser Phe Arg Ser Leu Leu Ala Leu Ser Gly Leu Val Cys Thr Gly
                -20             -15             -10

Leu Ala Asn Val Ile Ser Lys Arg Ala Thr Leu Asp Ser Trp Leu Ser
            -5               1               5

Asn Glu Ala Thr Val Ala Arg Thr Ala Ile Leu Asn Asn Ile Gly Ala
            10              15              20

Asp Gly Ala Trp Val Ser Gly Ala Asp Ser Gly Ile Val Val Ala Ser
25              30              35                              40

Pro Ser Thr Asp Asn Pro Asp Tyr Phe Tyr Thr Trp Thr Arg Asp Ser
            45              50              55

Gly Leu Val Leu Lys Thr Leu Val Asp Leu Phe Arg Asn Gly Asp Thr
            60              65              70

Ser Leu Leu Ser Thr Ile Glu Asn Tyr Ile Ser Ala Gln Ala Ile Val
            75              80              85

Gln Gly Ile Ser Asn Pro Ser Gly Asp Leu Ser Ser Gly Ala Gly Leu
            90              95              100

Gly Glu Pro Lys Phe Asn Val Asp Glu Thr Ala Tyr Thr Gly Ser Trp
105             110             115                             120

Gly Arg Pro Gln Arg Asp Gly Pro Ala Leu Arg Ala Thr Ala Met Ile
            125             130             135

Gly Phe Gly Gln Trp Leu Leu Asp Asn Gly Tyr Thr Ser Thr Ala Thr
            140             145             150

Asp Ile Val Trp Pro Leu Val Arg Asn Asp Leu Ser Tyr Val Ala Gln
            155             160             165

Tyr Trp Asn Gln Thr Gly Tyr Asp Leu Trp Glu Val Asn Gly Ser
            170             175             180

Ser Phe Phe Thr Ile Ala Val Gln His Arg Ala Leu Val Glu Gly Ser
185             190             195                             200

Ala Phe Ala Thr Ala Val Gly Ser Ser Cys Ser Trp Cys Asp Ser Gln
            205             210             215

Ala Pro Glu Ile Leu Cys Tyr Leu Gln Ser Phe Trp Thr Gly Ser Phe
            220             225             230

Ile Leu Ala Asn Phe Asp Ser Ser Arg Ser Gly Lys Asp Ala Asn Thr
            235             240             245

Leu Leu Gly Ser Ile His Thr Phe Asp Pro Glu Ala Ala Cys Asp Asp
            250             255             260

Ser Thr Phe Gln Pro Cys Ser Pro Arg Ala Leu Ala Asn His Lys Glu
265             270             275                             280

Val Val Asp Ser Phe Arg Ser Ile Tyr Thr Leu Asn Asp Gly Leu Ser
            285             290             295

Asp Ser Glu Ala Val Ala Val Gly Arg Tyr Pro Glu Asp Thr Tyr Tyr
            300             305             310

Asn Gly Asn Pro Trp Phe Leu Cys Thr Leu Ala Ala Ala Glu Gln Leu
```

```
                315                 320                 325
Tyr Asp Ala Leu Tyr Gln Trp Asp Lys Gln Gly Ser Leu Glu Val Thr
        330                 335                 340

Asp Val Ser Leu Asp Phe Phe Lys Ala Leu Tyr Ser Asp Ala Ala Thr
345                 350                 355                 360

Gly Thr Tyr Ser Ser Ser Ser Thr Tyr Ser Ser Ile Val Asp Ala
                365                 370                 375

Val Lys Thr Phe Ala Asp Gly Phe Val Ser Ile Val Glu Thr His Ala
            380                 385                 390

Ala Ser Asn Gly Ser Met Ser Glu Gln Tyr Asp Lys Ser Asp Gly Glu
            395                 400                 405

Gln Leu Ser Ala Arg Asp Leu Thr Trp Ser Tyr Ala Ala Leu Leu Thr
        410                 415                 420

Ala Asn Asn Arg Arg Asn Ser Val Val Pro Ala Ser Trp Gly Glu Thr
425                 430                 435                 440

Ser Ala Ser Ser Val Pro Gly Thr Cys Ala Ala Thr Ser Ala Ile Gly
                445                 450                 455

Thr Tyr Ser Ser Val Thr Val Thr Ser Trp Pro Ser Ile Val Ala Thr
            460                 465                 470

Gly Gly Thr Thr Thr Thr Ala Thr Pro Thr Gly Ser Gly Ser Val Thr
        475                 480                 485

Ser Thr Ser Lys Thr Thr Ala Thr Ala Ser Lys Thr Ser Thr Thr Thr
        490                 495                 500

Arg Ser Gly Met Ser Leu
505                 510

<210> SEQ ID NO 2
<211> LENGTH: 66
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22,23,25,26,28,29,31,32,34,35,37,38,40,41
<223> OTHER INFORMATION: n= a, c, g or t

<400> SEQUENCE: 2
gcaaatgtga tttccaagcg cnnsnnsnns nnsnnsnnsn nsgcgacctt ggattcatgg    60
ttgagc                                                              66

<210> SEQ ID NO 3
<211> LENGTH: 63
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22,23,25,26,28,29,31,32,34,35,37,38
<223> OTHER INFORMATION: n = a, c, g or t

<400> SEQUENCE: 3
gcaaatgtga tttccaagcg cnnsnnsnns nnsnnsnnsg cgaccttgga ttcatggttg    60
agc                                                                 63

<210> SEQ ID NO 4
<211> LENGTH: 60
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<222> LOCATION: 22,23,25,26,28,29,31,32,34,35
<223> OTHER INFORMATION: n = a, c, g or t

<400> SEQUENCE: 4
gcaaatgtga tttccaagcg cnnsnnsnns nnsnnsgcga ccttggattc atggttgagc      60

<210> SEQ ID NO 5
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22,23,25,26,28,29,31,32
<223> OTHER INFORMATION: n = a, c, g or t

<400> SEQUENCE: 5
gcaaatgtga tttccaagcg cnnsnnsnns nnsgcgacct tggattcatg gttgagc        57

<210> SEQ ID NO 6
<211> LENGTH: 54
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22,23,25,26,28,29
<223> OTHER INFORMATION: n = a, c, g or t

<400> SEQUENCE: 6
gcaaatgtga tttccaagcg cnnsnnsnns gcgaccttgg attcatggtt gagc           54

<210> SEQ ID NO 7
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22,23,25,26
<223> OTHER INFORMATION: n = a, c, g or t

<400> SEQUENCE: 7
gcaaatgtga tttccaagcg cnnsnnsgcg accttggatt catggttgag c              51

<210> SEQ ID NO 8
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22,23
<223> OTHER INFORMATION: n = a, g, c or t

<400> SEQUENCE: 8
gcaaatgtga tttccaagcg cnnsgcgacc ttggattcat ggttgagc                  48

<210> SEQ ID NO 9
<211> LENGTH: 21
<212> TYPE: DNA
```

```
<213> ORGANISM: Artificial Sequence
<220> FEATURE:
<223> OTHER INFORMATION: Primer
      n = a, g, c, or t

<400> SEQUENCE: 9
gcgcttggaa atcacatttg c                                              21

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tcaagaatag ttcaaacaag aaga                                           24

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cttttcggtt agagcggatg                                                20

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
cgcacgagat ctgcaatgtc gttccgatct cta                                 33

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
cagccggtcg actcacagtg acataccaga gcg                                 33

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
gaatgacttg gttgacgcgt caccagtcac                                     30

<210> SEQ ID NO 15
<211> LENGTH: 68
<212> TYPE: DNA
<213> ORGANISM: Artificial Sequence
<220> FEATURE:
<223> OTHER INFORMATION: Primer

<400> SEQUENCE: 15
``` gggatcatg ataggactag ccatattaat gaagggcata taccacgcct tggacctgcg    60
ttatagcc                                                            68

<210> SEQ ID NO 16
<211> LENGTH: 50
<212> TYPE: DNA
<213> ORGANISM: Artificial Sequence
<220> FEATURE:
<223> OTHER INFORMATION: Primer

<400> SEQUENCE: 16
gtgatttcca gcggtgcccg ccgtccacgt ccgcgacctt ggattcatgg              50

<210> SEQ ID NO 17
<211> LENGTH: 50
<212> TYPE: DNA
<213> ORGANISM: Artificial Sequence
<220> FEATURE:
<223> OTHER INFORMATION: Primer

<400> SEQUENCE: 17
gtgatttcca gcggtccccg ccgtccacgt ccgcgacctt ggattcatgg              50

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gtagcattgt atgtgccgtg aagac                                         25

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
accgtcgtaa ctgcgtcgtg cctgc                                         25

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
gtctcagtga cagctgcgct gttgcggtg                                     29

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
ccactacgac gtgcaccccc actgg                                         25

<210> SEQ ID NO 22
<211> LENGTH: 26

```
<212> TYPE: DNA
<213> ORGANISM: Artificial Sequence
<220> FEATURE:
<223> OTHER INFORMATION: Primer

<400> SEQUENCE: 22
ctacgacggc ttgccccact ggatcc                                               26

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
cgacggctac ctgcactgga tccggc                                               26

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
tggattcatg gttgtgtaac gaagcgacc                                            29

<210> SEQ ID NO 25
<211> LENGTH: 7
<212> TYPE: PRT
<213> ORGANISM: Artificial Sequence
<220> FEATURE:
<223> OTHER INFORMATION: Peptide

<400> SEQUENCE: 25

Ala Cys Gly Pro Ser Thr Ser
 1               5

<210> SEQ ID NO 26
<211> LENGTH: 7
<212> TYPE: PRT
<213> ORGANISM: Artificial Sequence
<220> FEATURE:
<223> OTHER INFORMATION: Peptide

<400> SEQUENCE: 26

Ala Cys Pro Gly Thr Ser Thr
 1               5

<210> SEQ ID NO 27
<211> LENGTH: 7
<212> TYPE: PRT
<213> ORGANISM: Artificial Sequence
<220> FEATURE:
<223> OTHER INFORMATION: Peptide

<400> SEQUENCE: 27

Ala Cys Gly Thr Gly Thr Ser
 1               5

<210> SEQ ID NO 28
<211> LENGTH: 7
<212> TYPE: PRT
<213> ORGANISM: Artificial Sequence
<220> FEATURE:
<223> OTHER INFORMATION: Peptide
```

```
<400> SEQUENCE: 28

Ala Cys Thr Gly Ser Thr Gly
 1               5

<210> SEQ ID NO 29
<211> LENGTH: 8
<212> TYPE: PRT
<213> ORGANISM: Artificial Sequence
<220> FEATURE:
<223> OTHER INFORMATION: Peptide

<400> SEQUENCE: 29

Ala Cys Gly Pro Ser Thr Ser Gly
 1               5

<210> SEQ ID NO 30
<211> LENGTH: 8
<212> TYPE: PRT
<213> ORGANISM: Artificial Sequence
<220> FEATURE:
<223> OTHER INFORMATION: Peptide

<400> SEQUENCE: 30

Ala Cys Pro Gly Thr Ser Thr Gly
 1               5

<210> SEQ ID NO 31
<211> LENGTH: 8
<212> TYPE: PRT
<213> ORGANISM: Artificial Sequence
<220> FEATURE:
<223> OTHER INFORMATION: Peptide

<400> SEQUENCE: 31

Ala Cys Gly Thr Gly Thr Ser Ser
 1               5

<210> SEQ ID NO 32
<211> LENGTH: 8
<212> TYPE: PRT
<213> ORGANISM: Artificial Sequence
<220> FEATURE:
<223> OTHER INFORMATION: Peptide

<400> SEQUENCE: 32

Ala Cys Thr Gly Ser Thr Gly Thr
 1               5

<210> SEQ ID NO 33
<211> LENGTH: 6
<212> TYPE: PRT
<213> ORGANISM: Artificial Sequence
<220> FEATURE:
<223> OTHER INFORMATION: Peptide

<400> SEQUENCE: 33

Asn Val Ile Pro Pro Arg
 1               5

<210> SEQ ID NO 34
<211> LENGTH: 6
<212> TYPE: PRT
<213> ORGANISM: Artificial Sequence
<220> FEATURE:
<223> OTHER INFORMATION: Peptide
```

```
<400> SEQUENCE: 34

Asn Pro Pro Ile Arg Pro
1               5

<210> SEQ ID NO 35
<211> LENGTH: 6
<212> TYPE: PRT
<213> ORGANISM: Artificial Sequence
<220> FEATURE:
<223> OTHER INFORMATION: Peptide

<400> SEQUENCE: 35

Asn Val Ile Pro Arg Pro
1               5

<210> SEQ ID NO 36
<211> LENGTH: 6
<212> TYPE: PRT
<213> ORGANISM: Artificial Sequence
<220> FEATURE:
<223> OTHER INFORMATION: Peptide

<400> SEQUENCE: 36

Asn Val Ile Ser Arg Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Peptide

<400> SEQUENCE: 37

Asn Val Ile Pro Lys Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Peptide

<400> SEQUENCE: 38

Ala Ser Pro Pro Ser Thr Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Peptide

<400> SEQUENCE: 39

Ala Cys Pro Pro Ser Thr Ser
1               5

<210> SEQ ID NO 40
<211> LENGTH: 6
<212> TYPE: PRT
<213> ORGANISM: Artificial Sequence
<220> FEATURE:
<223> OTHER INFORMATION: Peptide

<400> SEQUENCE: 40
```

```
Pro Cys Ser Ala Gly Glu
 1               5
```

<210> SEQ ID NO 41
<211> LENGTH: 6
<212> TYPE: PRT
<213> ORGANISM: Artificial Sequence
<220> FEATURE:
<223> OTHER INFORMATION: Peptide

<400> SEQUENCE: 41

```
Pro Leu Ala Leu Ser Asp
 1               5
```

<210> SEQ ID NO 42
<211> LENGTH: 6
<212> TYPE: PRT
<213> ORGANISM: Artificial Sequence
<220> FEATURE:
<223> OTHER INFORMATION: Peptide

<400> SEQUENCE: 42

```
Leu Gly Val Thr Gly Glu
 1               5
```

<210> SEQ ID NO 43
<211> LENGTH: 7
<212> TYPE: PRT
<213> ORGANISM: Artificial Sequence
<220> FEATURE:
<223> OTHER INFORMATION: Peptide

<400> SEQUENCE: 43

```
Ala Gly Pro Leu Pro Ser Glu
 1               5
```

<210> SEQ ID NO 44
<211> LENGTH: 4
<212> TYPE: PRT
<213> ORGANISM: Artificial Sequence
<220> FEATURE:
<223> OTHER INFORMATION: Peptide

<400> SEQUENCE: 44

```
Leu Gly Pro Asp
 1
```

<210> SEQ ID NO 45
<211> LENGTH: 7
<212> TYPE: PRT
<213> ORGANISM: Artificial Sequence
<220> FEATURE:
<223> OTHER INFORMATION: Peptide

<400> SEQUENCE: 45

```
Ile Phe Glu Leu Thr Pro Arg
 1               5
```

GLUCOAMYLASES WITH N-TERMINAL EXTENSIONS

CROSS-REFERENCE TO RELATED APPLICATIONS

This application claims priority under 35 U.S.C. 119 of Danish applications PA 1998 01616 filed Dec. 7, 1998 and PA 1999 00409 filed Mar. 24, 1999, and of U.S. Provisional applications No. 60/111,674 filed Dec. 10, 1998 and No. 60/126,740 filed Mar. 29, 1999, the contents of which are fully incorporated herein by reference.

FIELD OF THE INVENTION

The present invention relates to a glucoamylase variant of a parent glucoamylase, a DNA sequence encoding the variant glucoamylase and a process using such variant enzyme for hydrolyzing starch.

More specifically, the present invention relates to a glucoamylase variant having improved thermostability.

BACKGROUND OF THE INVENTION

Glucoamylase (1,4-α-D-glucan glucohydrolase, EC 3.2.1.3) is an enzyme which catalyzes the release of D-glucose from the non-reducing ends of starch or related oligo- and polysaccharide molecules. Glucoamylases are produced by several filamentous fungi and yeasts, with those from Aspergillus being commercially most important.

Commercially, the glucoamylase enzyme is used to convert corn starch which is already partially hydrolyzed by an α-amylase to glucose. The glucose is further converted by glucose isomerase to a mixture composed almost equally of glucose and fructose. This mixture, or the mixture further enriched with fructose, is the commonly used high fructose corn syrup commercialized throughout the world. This syrup is the world's largest tonnage product produced by an enzymatic process. The three enzymes involved in the conversion of starch to fructose are among the most important industrial enzymes produced.

One of the main problems exist with regard to the commercial use of glucoamylase in the production of high fructose corn syrup is the relatively low thermal stability of glucoamylase. Glucoamylase is not as thermally stable as α-amylase or glucose isomerase and it is most active and stable at lower pH's than either α-amylase or glucose isomerase. Accordingly, it must be used in a separate vessel at a lower temperature and pH.

SUMMARY OF THE INVENTION

Thus, the object of the present invention is to improve properties of enzymes with glucoamylase activity, in particular to improve the thermal stability of such enzymes.

It has surprisingly been found that it is possible to significantly enhance the thermal stability of an enzyme with glucoamylase activity by linking a peptide extension to the N-terminal of the enzyme.

Consequently, in a first aspect the invention relates to a variant of a parent glucoamylase, which has a peptide extension at the N-terminus.

In the present context the term "peptide extension" is intended to indicate that a stretch of one or more consecutive amino acid residues has been added to the N-terminal end of the parent (mature) glucoamylase.

The term "mature glucoamylase" is used in its conventional meaning, i.e., to indicate the active form of the glucoamylase resulting after posttranslational and postsecretional processing (to trim glycosylation and remove N and/or C-terminal sequences, such as pre- and pro-peptide sequences) by the producer organism in question. More specifically this means that amino acid sequences such as the pre- and pro-peptide sequences, if present, have been removed from the initially translated glucoamylase, i.e., the unprocessed glucoamylase. A mature glucoamylase encompassed by the present definition is a glucoamylase cut (processed) by Tripeptidyl amino peptidase (TPAP), which cuts the A. niger glucoamylase (see SEQ ID NO: 1) at position 3, i.e., between Leu and Asp.

The term "parent glucoamylase" is intended to indicate the glucoamylase to be modified according to the invention. The parent glucoamylase may be a naturally-occurring (or wild type) glucoamylase or may be a variant thereof prepared by any suitable means. For instance, the parent glucoamylase may be a variant of a naturally-occurring glucoamylase which has been modified by substitution, deletion or truncation of one or more amino acid residues or by addition or insertion of one or more amino acid residues to the amino acid sequence of a naturally-occurring glucoamylase, typically in the structural part of the glucoamylase.

In other aspects the invention relates to a DNA sequence encoding a glucoamylase variant as defined above, a DNA construct, a recombinant expression comprising a DNA sequence of the invention, and a host cell harbouring a DNA sequence of the invention or a vector of the invention.

The glucoamylase variant of the invention may conveniently be used in a process for converting starch and accordingly, in yet other aspects the invention relates to a process for converting starch or partially hydrolyzed starch into syrup containing dextrose, said process including the step saccharifying starch hydrolyzate in the presence of a glucoamylase variant of the invention.

In final aspects, the invention provides a method for improving the thermostability of parent glucoamylase by making an extension at the N-terminus.

The inventors of the present invention have provided a number of improved variants of a parent glucoamylase with improved thermostability. The improved thermal stability is obtained by linking a peptide extension to a parent glucoamylase. This will be described in details below.

DETAILED DESCRIPTION OF THE INVENTION

Peptide Extension

As stated above it has surprisingly been found that a glucoamylase variant, in particular with improved thermostability, may be achieved when an appropriate peptide extension can be found at the N-terminus of the parent glucoamylase. The present invention is based on this finding.

In the context of the present invention "..can be found at the N-terminal.." means that the mature glucoamylase has a peptide extension at the N-terminal. In one embodiment the peptide extension is native to the parent glucoamylase, i.e., before posttranslational processing to remove the pro- and/or pre-sequence. Thus, the peptide extension may be the pre- and/or pro-sequence of the unprocessed parent glucoamylase, which is normally removed or cut off after expression and posttranslational processing.

In another embodiment the extension is a peptide at the N-terminal identical to the peptide sequence normally being cut of by the donor cell during processing, e.g., the pre- and/or pro-sequence. In most cases the peptide extension is different from the pre- and/or pro-sequence. This will be described further below.

In the case of the extension is linked to the N-terminal it may be done by means of any well-known protein engineering methods in the art.

The term "a glucoamylase variant with improved thermostability" means in the context of the present invention a glucoamylase variant, which has a higher $T_{1/2}$ (half-time) or residual enzymatic activity after a fix incubation period than the corresponding parent glucoamylase. The determination of thermostability, e.g., T½ and residual activity, is described below in the Materials and Method section.

The term "an appropriate peptide extension" is used to indicate that the peptide extension to be used is one, which is capable of effecting an improved thermostability as defined above. The "appropriateness" of the peptide extension may be checked by a comparative analysis of the thermostability of a modified glucoamylase variant to which the peptide extension has been linked and of the corresponding parent glucoamylase, respectively. The thermostability may, e.g., be determined by any suitable technique such as the thermostability assay described in the present application.

It is presently believed that the capability of the peptide extension of providing the desired effect such as improved thermostability depends on, e.g., the identity of the parent glucoamylase to be modified, the structure (including length) of the peptide extension, the impact of the peptide extension on the structure of the entire glucoamylase variant enzyme, the nature or functionality of amino acid residues of the peptide extension, etc. A prerequisite for the peptide extension being capable of providing the desired effect is, of course, that the glucoamylase variant containing the peptide extension is expressible in a suitable host organism. The following general considerations may be of relevance for the design of a suitable peptide extension:

Length of peptide extension: It has been found that peptide extensions containing varying numbers of amino acid residues are capable of providing the desired effect and thus, it is not possible to specify an exact number of amino acid residues to be present in the peptide extension to be used in accordance with the present invention. It is contemplated that the upper limit of the number of amino acid residues is determined, inter alia, on the impact of the peptide extension on the expression, the structure and/or the activity of the resulting modified glucoamylase variant.

The peptide extension may thus comprise 1–100 amino acid residues, preferably 1–50 amino acid residues, more preferably 1–20 and even more preferably 1–10 amino acid residues.

Stability: The peptide extension should preferably be chosen so as to provide a glucoamylase variant with an acceptable stability (e.g., structural stability and/or expression stability) or so as to not significantly reduce the structural stability of the glucoamylase variant. Although many peptide extensions are not believed to confer any substantial structural instability to the resulting glucoamylase variant, it may in certain instances and with certain parent glucoamylases be relevant to choose a peptide extension, which in itself can confer a structural stability to the modified glucoamylase enzyme. For instance, the peptide extension can increase the number of interactions and/or be covalently bound by adding cysteine bridges to from the N-terminal extension to the N-terminal residues as discussed below.

Nature of amino acid residues of the peptide extension: To obtain an improved interaction between the N-terminal residues and the N-terminal extension, the residues should preferably come from residues with low preference for α-helix making, and thus be used in the context of the present invention. This can be rationalised by the fact that if the N-terminal α-helix is prolonged N-terminally it would stick out of the structure with no contact to the N-terminal residues. A peptide extension according to the invention comprises an improved stability by improving the contact of the N-terminal residues to the N-terminal extension. Within a giving N-terminal extension the main part of residues must come from a group of non-helix makers. It is contemplated by using residues having α-helix propensities in N-terminal of the helix, and/or in the middle of the helix, and/or C-terminal part of the helix, lower or equal to one, the improvement of contact between N-terminal residues and the N-terminal extension will be optimal. Residues having propensities lower than one in the N-terminal part of the alpha-helix are of special interest as the extension are placed in the N-terminal part of the natural α-helix in the glucoamylase. Residues comprising M (Methionine), K (Lysine), H (Histidine), V (Valine), I (Isoleucine), Y (Tyrosine), C (Cysteine), F (Phenylalanine), T (Threonine), G (Glycine), N (Asparagine), P (Proline), S (Serine) and D (Aspartic acid) can be used in the present invention as non-α-helix makers.

In the context of the invention "N-terminal residues" mean the residues around the N-terminal residue, i.e., in a sphere of 18, 12 and/or 8 Å from the central of the N-terminal residue, and which is not a part of the N-terminal extension. More preferred, the extensions are within 10 Å but on the surface of the enzyme defined as the residues having a positive number in accessibility using the Connelly water accessible surface program ((version October 1988), reference W. Kabsch and C. Sander, Biopolymers 22 (1983) pp. 2577–2637.))

"Non-helix makers" are here defined by the data obtained from table 6.5 in ((Proteins: Creighton T. E. (1993)) where different propensities are described for the different amino acid residues.

Alternatively, an improved structural stability may be provided by introduction of cysteine bridges in the glucoamylases of the invention. For instance, a cysteine bridge between the peptide extension and the mature part of the glucoamylase may be established if at least one of the amino acid residues of the peptide extension is a cysteine residue which is located so as to be able to form a covalent binding to a cysteine residue in the mature part of the glucoamyalse variant. The positive effect of introducing a cysteine bridge is illustrated in Example 3. If no suitable cysteine is present in the mature glucoamylase, a cysteine may be inserted at a suitable location of said parent glucoamylase, conveniently by replacing an amino acid of the parent glucoamylase, which is considered unimportant for the activity.

Generally, the amino acid sequence of a peptide extension comprising a cysteine residue in the present invention can be referred to as:

wherein x independently represents one amino acid, preferably of the above mentioned non-α-helix makers, even more preferably with short side chains.

Between the carboxy-terminal side of the Cys and processed, naturally occurring N-terminal, there can be any number (n) of X residues larger or equal to 5, preferably between 5 and 100, even more preferably between 5 and 10, even more preferably 5.

Examples Are
ACGPSTS (SEQ ID NO: 25)
ACPGTST (SEQ ID NO: 26)
ACGTGTS (SEQ ID NO: 27)
ACTGSTG (SEQ ID NO: 28)
ACGPSTSG (SEQ ID NO: 29)
ACPGTSTG (SEQ ID NO: 30)
ACGTGTSS (SEQ ID NO: 31)
ACTGSTGT (SEQ ID NO: 32)

The native pro-peptide of a glucoamylase (e.g., the *A. niger* G1 or G2 AMG) is cleaved of by a kex2-like protease (dibasic protease). Thus, kex2 proteases are proteases capable of cleaving kex2 or kex2-like sites. Kex2 sites (see, e.g., Methods in Enzymology Vol 185, ed. D. Goeddel, Academic Press Inc. (1990), San Diego, Calif., "Gene Expression Technology") and kex2-like sites are di-basic recognition sites (i.e., cleavage sites) found between the pro-peptide encoding region and the mature region of some proteins.

Mutating this cleavage site may leave the N-terminal pro-peptide intact.

Examples
NVIPPR (SEQ ID NO: 33)
NPPIRP (SEQ ID NO: 34)
NVIPRP (SEQ ID NO: 35)

Another possibility is to delete or inactivate the kex2-like proteases encoding gene in the host chosen to express the glucoamylase gene. This may also leave the N-terminal peptide extension intact.

Other genes encoding proteases involved in N-terminal processing such as a tripeptidyl aminopeptidase encoding gene might also be deleted or inactivated in the host of interest for expression.

N-terminal residues for cysteine variants are defined as the residues around the N-terminal residue, i.e., in a sphere of 18, 12 and/or 8 Å from the central of the N-terminal residue, and which is not a part of the N-terminal extension. Generally, the amino acid sequence for an extension comprising a cysteine residue in the present invention can be referred to as: x-C-x-x-x-x-x, wherein x independently represents one of the above mentioned non-α-helix makers.

In a specific embodiment, the glucoamylase variant comprises peptide extension, which is capable of forming a covalent binding to the mature part of the parent glucoamylase. In another specific embodiment, the glucoamylase variant comprises one or more cysteine residue in the peptide extension and a cysteine residue in the mature part of the parent glucoamylase in such a manner that said cysteine residues together form a cysteine bridge. In yet another specific embodiment, the cysteine residue in the mature part of the parent glucoamylase has been inserted or has substituted an amino acid residue of the parent glucoamylase. In an most preferred specific embodiment, the aspartic acid residue at a position corresponding to position 375 or the glutamic acid at a position corresponding to position 299 or the serine residue at a position corresponding to position 431 or the alanine residue at a position corresponding to position 471 or the alanine residue at a position corresponding to position 479 or the threonine residue at a position corresponding to position 480 or the proline residue at a position corresponding to position 481 or the serine residue at a position corresponding to position 8, has been substituted with a cysteine residue in the amino acid sequence of *Aspergillus niger* G1 glucoamylase.

Specifically, the peptide extension linked to the parent glucoamylase may advantageously be one of the following extensions:

Asn-Val-Ile-Ser-Arg-Arg(NVISRR)(SEQ ID NO:36), or
Asn-Val-Ile-Pro-Lys-Arg(NVIPKR)(SEQ ID NO:37), or
Ala-Ser-Pro-Pro-Ser-Thr-Ser(ASPPSTS)(SEQ ID NO:38), or
Ala-Cys-Pro-Pro-Ser-Thr-Ser(ACPPSTS)(SEQ ID NO:39), or
Pro-Cys-Ser-Ala-Gly-Glu(PCSAGE)(SEQ ID NO:40), or
Pro-Leu-Ala-Leu-Ser-Asp(PLALSD)(SEQ ID NO:41), or
Leu-Gly-Val-Thr-Gly-Glu(LGVTGE)(SEQ ID NO:42), or
Ala-Gly-Pro-Leu-Pro-Ser-Glu(AGPLPSE)(SEQ ID NO:43), or
Leu-Gly-Pro-Asp(LGPD)(SEQ ID NO:44), or
Ile-Phe-Glu-Leu-Thr-Pro-Arg(IFELTPR)(SEQ ID NO:45), or
Ile-Ser-Asn(ISN), or
Met-Asn(MN).

In the present context, a tripeptidyl aminopeptidase (TPAP) is intended to indicate an aminopeptidase which cleaves tripeptides from the N-terminus of a peptide or protein sequence, such as an extended amino acid sequence found in a prohormone or proenzyme. The tripeptidyl aminopeptidase (TPAP) has in some cases been found to lead to a reduced stability when cleaving tripeptide fragments from unsubstituted N-termini of peptides, oligonucleutides, or proteins. More specific, the tripeptidyl aminopeptidase cleavage of N-termini reduces the stability of glucoamylase enzymes. Accordingly, the invention also relates to a variant of a parent glucoamylase, wherein the peptide extension is capable of preventing a tripeptidyl aminopeptidase (TPAP) cleavage of the glucoamylase enzyme.

Methods of Linking a Peptide Extension to a Parent Glucoamylase

Although a variant of the invention may be obtained by adding (fusing or inserting) a synthetically produced peptide extension into the parent glucoamylase enzyme in question, it is presently preferred that the glucoamylase variant of the invention is prepared by i) modifying the nucleotide, preferably DNA, sequence encoding the parent glucoamylase so as to encode the desired peptide extension applied to the N-terminal end of the parent glucoamylase (e.g. by inserting a nucleic acid (preferably DNA) sequence encoding the peptide extension at the relevant location in the nucleic acid (preferably DNA) sequence encoding the parent glucoamylase), ii) expressing the resulting modified nucleic acid (preferably DNA) sequence in a suitable expression system, and iii) recovering the resulting glucoamylase variant.

In the present context, the term "linked at" is intended to indicate that the extension is fused to the N-terminal end (e.g. last amino acid residue) of the mature glucoamylase.

Many glucoamyalses are expressed as "preproglucoamylases", i.e., as glucoamyalses consisting of the mature glucoamylase, a secretory signal peptide (i.e., prepeptide) and a pro-peptide. The prepro-glycoamylase is processed intracellularly to be secreted into the fermentation medium, from which the mature glucoamylase can be isolated and/or purified. Adding the peptide extension to the parent glucoamylase can be carried out by linking nucleic acid sequences encoding the desired peptide extensions upstream (for N-terminal peptide extensions) to the DNA sequence encoding the parent glucoamylase.

The insertion should be performed in such a way that the desired glucoamylase variant (i.e., having the desired peptide extensions(s)) is expressed and secreted by the host cell after transcription, translation, and processing of the glucoamylase variant. The term "processing" means in this context removal of pre- and pro-peptides (except, of course, when the pro-peptide is identical to the desired peptide extension. This will be dealt with further below).

In most cases it is possible to extend the parent glucoamylase by inserting a DNA sequence encoding the peptide extension between the DNA sequence encoding the pro-peptide or the prepeptide (if no prosequence is present) and the DNA sequence encoding the mature glucoamylase.

The insertion/addition of a DNA sequence encoding the peptide extension can be carried out by any standard techniques known by any skilled person in the field of molecular biology, cf., e.g. Sambrook et al., 1989). This include, e.g., the polymerase chain reaction (PCR) using specific primers, for instance described in U.S. Pat. No. 4,683,202 or R. K. Saiki et al., (1988), Science, 239, 487–491. How to provide for the expression and secretion of adjacent DNA sequence (s) will be described below.

While care must be exerted to select a proper expression system for producing a glucoamylase variant of the invention (in particular when a modified DNA sequence is used for the production), it has been found that a glucoamylase variant according to the invention (having an improved thermal stability) may be obtained by expressing a DNA sequence encoding the parent glucoamylase enzyme in question in an expression system which is incapable of processing the translated polypeptide in the normal manner, and thereby results in the production of an glucoamylase which comprises a part of or the entire propeptide or a similar peptide sequence associated with the mature protein prior to its processing. In this case, the propeptide or similar peptide sequence constitutes the peptide extension. The pro-peptide or similar peptide sequence may be heterologous or homologous to the parent glucoamylase and can be present in the N-terminal of the parent glucoamylase. The production of a glucoamylase variant according to the invention using this latter technique is described further below.

Accordingly, if a suitable stretch of amino acids is already encoded in the prepro form of the parent glucoamylase and this stretch of amino acids is cut off in the processing of the glucoamylase by a given expression system, the peptide extension can be applied by changing the expression host system to a system in which said processing of said stretch of amino acids does not occur. In such a case the secretory signal pre-peptide will be cut off during or after the secretion, resulting in a modified glucoamylase consisting of the parent glucoamylase comprising the pro-peptide or part thereof or a similar peptide sequence encoded by the corresponding DNA sequence, i.e. a glucoamylase being extended at the N-terminus.

Yeast cells have been found of particular use for applying peptide extensions (in the form of the propeptide or a part thereof) to parent fungal glucoamyalses enzymes, in particular the *Aspergillus niger* glucoamylase enzyme.

In an highly preferred embodiment the peptide extension is designed and applied by means of random mutagenesis according to the following principle:

a) subjecting a DNA sequence encoding the parent gluciamylase enzyme with a peptide extension to localized random mutagenesis in the peptide extension or in a of the N-terminal end of the parent glucoamylase, b) expressing the mutated DNA sequence obtained in step a) in a host cell, and c) screening for host cells expressing a mutated glucoamyalse enzyme which has an improved performance as compared to the parent glucoamyalse enzyme.

By this approach a number of highly advantageous peptide additions have been created. The localized random mutagenesis may be performed essentially as described in WO 95/22615. More specifically, the mutagenesis is performed under conditions in which only one or more of the above areas are subjected to mutagenesis. Especially for mutagenizing large peptide extensions, it may be relevant to use PCR generated mutagenesis (e.g. as described by Deshler 1992 or Leung et al., 1989), in which one or more suitable oligonucleotide probes are used which flanks the area to be mutagenized. For mutagenesis of shorter peptide extensions, it is more preferably perform the localized random mutagenesis by use of doped or spiked oligonucleotides. The doping or spiking is used, e.g., to avoid codons for unwanted amino acid residues or to increase the likelihood that a particular type of amino acid residue, such as a positively charged or hydrophobic amino acid residue, is introduced at a desired position.

Subsequent to the mutagenesis the mutated DNA is expressed by culturing a suitable host cell carrying the DNA sequence under conditions allowing expression to take place. The host cell used for this purpose may be one which has been transformed with the mutated DNA sequence, optionally present on a vector, or one which carried the DNA sequence encoding the parent enzyme during the mutagenesis treatment. Examples of suitable host cells are given below, and is preferably a host cell which is capable of secreting the mutated enzyme (enabling an easy screening). Yeast cells, such as cells of *S. cereviciae,* have been found to be suitable host cells.

Parent Glucoamylases

Parent glucoamylase contemplated according to the present invention include fungal glucoamylases, in particular fungal glucoamylases obtainable from an Aspergillus strain, such as an *Aspergillus niger* or *Aspergillus awamori* glucoamylases and variants or mutants thereof, homologous glucoamylases, and further glucoamylases being structurally and/or functionally similar to SEQ ID NO: 1. Specifically contemplated are the *Aspergillus niger* glucoamylases G1 and G2 disclosed in Boel et al. (1984), "Glucoamylases G1 and G2 from *Aspergillus niger* are synthesized from two different but closely related mRNAs", EMBO J. 3 (5), p. 1097–1102,. The G2 glucoamylase is disclosed in SEQ ID NO: 1.

Commercial Parent Glucoamylases

Commercially available parent glucoamylases include AMG from Novo Nordisk, and also glucoamylase from the companies Genencor, Inc. USA, and Gist-Brocades, Delft, The Netherlands.

Parent Homologous Glucoamylases

The homology of the parent glucoamylase is determined as the degree of similarity between two protein sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443–453). Using GAP with the following settings for polypeptide sequence comparison: GAP creation penalty of 3.0 and GAP extension penalty of 0.1, the mature part of a polypeptide encoded by an analogous DNA sequence of the invention exhibits a degree of identity preferably of at least 80%, at least 90%, more preferably at least 95%, more preferably at least 97%, and most preferably at least 99% with the mature part of the amino acid sequence shown in SEQ ID NO 1.

In a preferred embodiment the variant of the invention has improved thermal stability within the temperature interval from about 60–80° C., preferably 63–75° C., at a pH of 4–5, in particular 4.2–4.7, using e.g. maltodextrin as the substrate.

In another preferred embodiment, the parent homologous glucoamylase comprises a glucoamylase from a microorganism. In a more preferred embodiment, the microorganism comprises Eubacteria, Archaebacteria, fungi, algae and protozoa, and in an yet more preferred embodiment, the parent homologous glucoamylase is derived from a filamentous fungi.

In an highly preferred embodiment the parent glycoamylase is the *Aspergillus niger* G1 glucoamylase (Boel et al. (1984), EMBO J. 3 (5), p. 1097–1102. The parent glycoamylase may be a truncated glucoamylase.

Methods for Preparing Glucoamylase Variants

Several methods for introducing mutations into genes are known in the art. After a brief discussion of the cloning of glucoamylase-encoding DNA sequences, methods for generating mutations at specific sites within the glucoamylase-encoding sequence will be discussed.

Cloning a DNA sequence encoding a glucoamylaseCloning a DNA sequence encoding an a-amylaseCloning a DNA sequence encoding an a-amylaseCloning a DNA sequence encoding an a-amylaseCloning a DNA sequence encoding an a-amylase The DNA sequence encoding a parent glucoamylase may be isolated from any cell or microorganism producing the glucoamylase in question, using various methods well known in the art. First, a genomic DNA and/or cDNA library should be constructed using chromosomal DNA or messenger RNA from the organism that produces the glucoamylase to be studied. Then, if the amino acid sequence of the glucoamylase is known, labeled oligonucleotide probes may be synthesized and used to identify glucoamylase-encoding clones from a genomic library prepared from the organism in question. Alternatively, a labelled oligonucleotide probe containing sequences homologous to another known glucoamylase gene could be used as a probe to identify glucoamylase-encoding clones, using hybridization and washing conditions of lower stringency.

Yet another method for identifying glucoamylase-encoding clones would involve inserting fragments of genomic DNA into an expression vector, such as a plasmid, transforming glucoamylase-negative bacteria with the resulting genomic DNA library, and then plating the transformed bacteria onto agar containing a substrate for glucoamylase (i.e. maltose), thereby allowing clones expressing the glucoamylase to be identified.

Alternatively, the DNA sequence encoding the glucoamylase may be prepared synthetically by established standard methods, e.g. the phosphoroamidite method described S. L. Beaucage and M. H. Caruthers, (1981), Tetrahedron Letters 22, p. 1859–1869, or the method described by Matthes et al., (1984), EMBO J. 3, p. 801–805. In the phosphoroamidite method, oligonucleotides are synthesized, e.g. in an automatic DNA synthesizer, purified, annealed, ligated and cloned in appropriate vectors. Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487–491.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent glucoamyalse during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus;* and gram-negative bacteria such as *E. coli.* The mutated DNA sequence may further comprise a DNA sequence encoding functions permitting expression of the mutated DNA sequence.

Site-directed Mutagenesis

Once a glucoamylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the glucoamylase-encoding sequence, is created in a vector carrying the glucoamylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646–639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into glucoamylase-encoding DNA sequences is described in Nelson and Long, (1989), Analytical Biochemistry 180, p. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Further, Sierks. et al., (1989) "Site-directed mutagenesis at the active site Trp120 of *Aspergillus awamori* glucoamylase. Protein Eng., 2, 621–625; Sierks et al., (1990), "Determination of *Aspergillus awamori* glucoamylase catalytic mechanism by site-directed mutagenesis at active site Asp176, Glu179, and Glu180". Protein Eng. vol. 3, 193–198; also describes site-directed mutagenesis in an Aspergillus glucoamylase.

Random Mutagenesis

Random mutagenesis is suitably performed either as localised or region-specific random mutagenesis in at least three parts of the gene translating to the amino acid sequence shown in question, or within the whole gene. The random mutagenesis of a DNA sequence encoding a parent glucoamylase may be conveniently performed by use of any method known in the art. In relation to the above, a further aspect of the present invention relates to a method for generating a variant of a parent glucoamylase, wherein the variant exhibits increased thermal stability relative to the parent, the method comprising:

(a) subjecting a DNA sequence encoding the parent glucoamylase to random mutagenesis, (b) expressing the mutated DNA sequence obtained in step (a) in a host cell, and (c) screening for host cells expressing a glucoamylase variant which has an altered property (i.e. thermal stability) relative to the parent glucoamylase. Step (a) of the above method of the invention is preferably performed using doped primers, as described in the working examples herein (vide infra). For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions. Examples of a physical or chemical mutagenizing agent suitable for the present purpose include ultraviolet (UV) ir-radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties. When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the glucoamylase enzyme by any published technique, using e.g. PCR, LCR or any DNA polymerase and ligase as deemed appropriate. Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided. When PCR-generated mutagenesis is used, either a chemically treated or non-treated gene encoding a parent glucoamylase is subjected to PCR under conditions that increase the mis-incorporation of nucleotides (Deshler 1992; Leung et al., Technique, Vol.1, 1989, pp. 11–15). A mutator strain of *E. coli* (Fowler et al., Molec. Gen. Genet., 133, 1974, pp. 179–191), *S. cereviseae* or any other microbial organism may be used for the random mutagenesis of the DNA encoding the glucoamylase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism. The DNA sequence to be mutagenized may be conveniently present in a genomic or cDNA library prepared from an organism expressing the parent glucoamylase. Alternatively, the DNA sequence may be present on a suitable vector such as a plasmid or a bacteriophage, which as such may be incubated with or other-wise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence. In some cases it may be convenient to amplify the mutated DNA sequence prior to performing the expression step b) or the screening step c) . Such amplification may be performed in accordance with methods known in the art, the presently preferred method being PCR-generated amplification using oligonucleotide primers prepared on the basis of the DNA or amino acid sequence of the parent enzyme. Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus;* and gram-negative bacteria such as *E. coli.* The mutated DNA sequence may further comprise a DNA sequence encoding functions permitting expression of the mutated DNA sequence.

Localized Random Mutagenesis

The random mutagenesis may be advantageously localized to a part of the parent glucoamylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Expression of Glucoamylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a glucoamylase variant of the invention may be any vector, which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a glucoamylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419–434, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a glucoamylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual,* 2nd Ed., Cold Spring Harbor, 1989).

Host Cells

The cell of the invention, either comprising a DNA construct or an expression vector of the invention as defined above, is advantageously used as a host cell in the recombinant production of a glucoamylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E. coli.* The transformation of the bacteria may, for instance, be effected by protoplast transformation or by using competent cells in a manner known per se.

The yeast organism may favorably be selected from a species of Saccharomyces or Schizosaccharomyces, e.g. *Saccharomyces cerevisiae.*

The host cell may also be a filamentous fungus e.g. a strain belonging to a species of Aspergillus, most preferably *Aspergillus oryzae* or *Aspergillus niger,* or a strain of Fusarium, such as a strain of *Fusarium oxysporium, Fusarium graminearum* (in the perfect state named *Gribberella zeae,* previously *Sphaeria zeae,* synonym with *Gibberella roseum* and *Gibberella roseum* f. sp. *cerealis*), or *Fusarium sulphureum* (in the prefect state named *Gibberella puricaris,* synonym with *Fusarium trichothecioides, Fusarium bactridioides, Fusarium sambucium, Fusarium roseum,* and *Fusarium roseum* var. *graminearum*), *Fusarium cerealis* (synonym with *Fusarium crokkwellnse*), or *Fusarium venenatum.*

In a preferred embodiment of the invention the host cell is a protease deficient of protease minus strain.

This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of Aspergillus as a host micro-organism is described in EP 238 023 (Novo Nordisk A/S), the contents of which are hereby incorporated by reference.

Method of Producing the Glucoamylase Variant of the Invention

In a yet further aspect, the present invention relates to a method of producing a glucoamylase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the glucoamylase variant of the invention. Suitable media are available from commercial suppliers or may be prepared according to published recipes (e.g. as described in catalogues of the American Type Culture Collection).

The glucoamylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Starch Conversion

The present invention provides a method of using glucoamylase variants of the invention for producing glucose and the like from starch. Generally, the method includes the steps of partially hydrolyzing precursor starch in the presence of α-amylase and then further hydrolyzing the release of D-glucose from the non-reducing ends of the starch or related oligo- and polysaccharide molecules in the presence of glucoamylase by cleaving α-(1→4) and α-(1→6) glucosidic bonds.

The partial hydrolysis of the precursor starch utilizing α-amylase provides an initial breakdown of the starch molecules by hydrolyzing internal α-(1→4)-linkages. In commercial applications, the initial hydrolysis using α-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately one hour at a temperature of 85° to 90° C. to derive a dextrose equivalent (D.E.) of 10 to 15.

The step of further hydrolyzing the release of D-glucose from the non-reducing ends of the starch or related oligo- and polysaccharides molecules in the presence of glucoamylase is normally carried out in a separate tank at a reduced temperature between 30° and 60° C. Preferably the temperature of the substrate liquid is dropped to between 55° and 60° C. The pH of the solution is dropped from 6 to 6.5 to a range between 3 and 5.5. Preferably, the pH of the solution is 4 to 4.5. The glucoamylase is added to the solution and the reaction is carried out for 24–72 hours, preferably 36–48 hours.

By using a thermostable glucoamylase variant of the invention saccharification processes may be carried out at a higher temperature than traditional batch saccharification processes. According to the invention saccharification may be carried out at temperatures in the range from above 60–80° C., preferably 63–75° C. This apply both for traditional batch processes (described above) and for continuous saccharification processes.

Actually, continuous saccharification processes including one or more membrane separation steps, i.e. filtration steps, must be carried out at temperatures of above 60° C. to be able to maintain a reasonably high flux over the membrane or to minimize microbial contamination. Therefore, the thermostable variants of the invention provides the possibility of carrying out large scale continuous saccharification processes at a fair price and/or at a lower enzyme protein dosage within and period of time acceptable for industrial saccharification processes. According to the invention the saccharification time may even be shortened.

The activity of the glucoamylase variant (e.g. AMG variant) of the invention is generally substantially higher at temperatures between 60° C.–80° C. than at the traditionally used temperature between 30–60° C. Therefore, by increasing the temperature at which the glucoamylase operates the saccharification process may be carried out within a shorter period of time.

Further, by improving the thermal stability the $T_{1/2}$ (half-time, as defined in the "Materials and Methods" section) is improved. As the thermal stability of the glucoamylase variants of the invention is improved a minor amount of glucoamylase need to be added to replace the glucoamylase being inactivated during the saccharification process. More glucoamylase is maintained active during saccharification process according to the present invention. Furthermore, the risk of microbial contamination is also reduced when carrying the saccharification process at temperature above 63° C.

An example of saccharification process wherein the glucoamylase variants of the invention may be used include the processes described in JP 3-224493; JP 1-191693 ;JP 62-272987; and EP 452,238.

The glucoamylase variant(s) of the invention may be used in the present inventive process in combination with an enzyme that hydrolyzes only α-(1→6)-glucosidic bonds in molecules with at least four glucosyl residues. Preferentially, the glucoamylase variant of the invention can be used in combination with pullulanase or isoamylase. The use of isoamylase and pullulanase for debranching, the molecular properties of the enzymes, and the potential use of the enzymes with glucoamylase is set forth in G. M. A. van Beynum et al., Starch Conversion Technology, Marcel Dekker, New York, 1985, 101–142.

In a further aspect the invention relates to the use of a glucoamylase variant of the invention in a starch conversion process.

Further, the glucoamylase variant of the invention may be used in a continuous starch conversion process including a continuous saccharification step.

The glucoamylase variants of the invention may also be used in immobilised form. This is suitable and often used for producing speciality syrups, such as maltose syrups, and further for the raffinate stream of oligosaccharides in connection with the production of fructose syrups.

The glucoamylase of the invention may also be used in a process for producing ethanol for fuel or beverage or may be used in a fermentation process for producing organic compounds, such as citric acid, ascorbic acid, lysine, glutamic acid.

Finally, the invention also relates to a method for improving the thermostability of a parent glucoamylase by making an extension at the N-terminus. In an important embodiment, the extension comprises a peptide extension.

Material and Methods

Material

Enzymes

AMG G1: *Aspergillus niger* glucoamylase G1 disclosed in Boel et al. (1984), EMBO J. 3 (5), 1097–1102, available from Novo Nordisk.AMG G2: Truncated *Aspergillus niger* glucoamylase G1 shown in SEQ ID No. 1, available from Novo Nordisk)

Host cell

A. oryzae JaL 125: *Aspergillus oryzae* IFO 4177 available from Institute for Fermentation, Osaka; 17–25 Juso Hammachi 2-Chome Yodogawa-ku, Osaka, Japan, having the alkaline protease gene named "alp" (described by Murakami K et al., (1991), Agric. Biol. Chem. 55, p. 2807–2811) deleted by a one step gene replacement method (described by G. May in "Applied Molecular Genetics of Filamentous Fungi" (1992), p. 1–25. Eds. J. R. Kinghorn and G. Turner; Blackie Academic and Professional), using the *A. oryzae* pyrG gene as marker. Strain JaL 125 is further disclosed in WO 97/35956 (Novo Nordisk).

Micro-organisms

Strain: *Saccharomyces cerevisiae* YNG318: MATαleu2-Δ2 ura3-52 his4-539 pep4-Δ1[cir+]

Plasmids pLaC103: Plasmid encoding the truncated *Aspergillus niger* glucoamylase G2.pJSO026: (*S. cerevisiae* expression plasmid) (J. S. Okkels, (1996) "A URA3-promoter deletion in a pYES vector increases the expression level of a fungal lipase in *Saccharomyces cerevisiae*. Recombinant DNA Biotechnology III: The Integration of Biological and Engineering Sciences, vol. 782 of the Annals of the New York Academy of Sciences) More specifically, the expression plasmid pJSO26, is derived from pYES 2.0 by replacing the inducible GAL1-promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419–434), and deleting a part of the URA3 promoter.

Methods

Transformation of *Saccharomyces cerevisiae* YNG318

The DNA fragments and the opened vectors were mixed and transformed into the yeast *Saccharomyces cerevisiae* YNG318 by standard methods.

Determination of AGU Activity

One Novo Amyloglucosidase Unit (AGU) was defined as the amount of enzyme which hydrolyzes 1 micromole maltose per minute under the following standard conditions:

Substrate . . . maltose
Temperature . . . 25° C.
pH . . . 4.3 (acetate buffer)
Reaction time . . . 30 minutes A detailed description of the analytical method (AF22) is available on request.

Transformation of *Aspergillus oryzae* (General Procedure)

100 ml of YPD (Sherman et al., (1981), Methods in Yeast Genetics, Cold Spring Harbor Laboratory) were inoculated with spores of *A. oryzae* and incubated with shaking for about 24 hours. The mycelium was harvested by filtration through miracloth and washed with 200 ml of 0.6 M $MgSO_4$. The mycelium was suspended in 15 ml of 1.2 M $MgSO_4$, 10 mM $NaH_2PO_4$, pH 5.8. The suspension was cooled on ice and 1 ml of buffer containing 120 mg of Novozym™ 234 was added. After 5 min., 1 ml of 12 mg/ml BSA (Sigma type H25) was added and incubation with gentle agitation continued for 1.5–2.5 hours at 37° C. until a large number of protoplasts are visible in a sample inspected under the microscope.

The suspension was filtered through miracloth, the filtrate transferred to a sterile tube and overlayed with 5 ml of 0.6 M sorbitol, 100 mM Tris-HCl, pH 7.0. Centrifugation was performed for 15 min. at 1000 g and the protoplasts were collected from the top of the $MgSO_4$ cushion. 2 volumes of STC (1.2 M sorbitol, 10 mM Tris-HCl, pH 7.5, 10 mM $CaCl_2$) were added to the protoplast suspension and the mixture is centrifugated for 5 min. at 1000 g. The protoplast pellet was resuspended in 3 ml of STC and repelleted. This was repeated. Finally, the protoplasts were resuspended in 0.2–1 ml of STC.

100 μl of protoplast suspension were mixed with 5–25 μg of p3SR2 (an *A. nidulans* amdS gene carrying plasmid described in Hynes et al., Mol. and Cel. Biol., Vol. 3, No. 8, 1430–1439, Aug. 1983) in 10 μl of STC. The mixture was left at room temperature for 25 min. 0.2 ml of 60% PEG 4000 (BDH 29576), 10 mM $CaCl_2$ and 10 mM Tris-HCl, pH 7.5 was added and carefully mixed (twice) and finally 0.85 ml of the same solution were added and carefully mixed. The mixture was left at room temperature for 25 min., spun at 2.500 g for 15 min. and the pellet was resuspended in 2 ml of 1.2M sorbitol. After one more sedimentation the protoplasts were spread on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth. After incubation for 4–7 days at 37° C. spores were picked, suspended in sterile water and spread for single colonies. This procedure is repeated and spores of a single colony after the second re-isolation were stored as a defined transformant.

Fed Batch Fermentation Fed batch fermentation is performed in a medium comprising maltodextrin as a carbon source, urea as a nitrogen source and yeast extract. The fed batch fermentation is performed by inoculating a shake flask culture of *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration. Further purification may be done by anionexchange chromatographic methods known in the art.

Purification

The culture broth is filtrated and added ammoniumsulphate (AMS) to a concentration of 1.7 M AMS and pH is adjusted to pH 5. Precipitated material is removed by centrifugation on the solution containing glucoamylase activity is applied on a Toyo Pearl Butyl column previously equilibrated in 1.7 M AMS, 20 mM sodium acetate, pH 5. Unbound material is washed out with the equilibration buffer. Bound proteins are eluted with 10 mM sodium acetate, pH 4.5 using a linear gradient from 1.7–0 M AMS over 10 column volumes. Glucoamylase containing fractions are collected and dialysed against 20 mM sodium acetate, pH 4.5.

Thermal Stability Determination of Variant of the Invention

The thermal stability of variants of the invention is tested using the following method: 950 microliter 50 mM sodium acetate buffer (pH 4.3) (NaOAc) is incubated for 5 minutes at 70° C. 50 microliter enzyme in buffer (4 AGU/ml) is added. 2×40 microliter samples are taken at 0, 5, 20 and/or 40 minutes, respectively, and chilled on ice. The activity (AGU/ml) measured before incubation (0 minutes) is used as reference (100%). The decline in percent is calculated as a function of the incubation time.

$T_{1/2}$ (Half-life) of the Glucoamylase

The $T_{1/2}$ is measured by incubating the glucoamylase (0.18–0.36 AG/g DS) in question in 30% 10 DE maltodextrin at pH 4.5 at the temperature in question (e.g. 70° C.) . Samples were withdrawn at set time intervals and further incubated at 50° C. for 24 hours to ensure that all substrate was hydrolysed, since maltodextrin might affect the activity assay. Incubation at 50° C. for 24 hours will not reduce the enzyme activity significantly. After incubation the samples were cooled and residual enzyme activity measured by the pNPG method (as described below).

The % residual glucoamylase activity was determined at different times. $T_{1/2}$ was the period of time until which the % relative activity was decreased to 50%.

Residual Enzyme Activity (pNPG Method)
pNPG Reagent 0.2 g pNPG (p-nitrophenylglucopyranoside) was dissolved in 0.1 M acetate buffer (pH 4.3) and made up to 100 ml.

Borate Solution 3.8 g $Na_2B_4O_7.10\ H_2O$ was dissolved in Milli-Q water and made up to 100 ml.

AMG Standard

An aqueous enzyme solution containing a known amount of enzyme equivalent to 0.04 AGU/ml.

Samples might be diluted prior to analysis (1:1–1:2 with water). The following solutions were prepared:
HS: 0.5 ml sample+1 ml AMG standard+3 ml pNPG reagent
H: 0.5 ml sample+1 ml water+3 ml pNPG reagent
B: 0.5 ml sample+1 ml AMG standard+3 ml borate solution Place HS and H in a 50° C. water bath. After 2 hours, 3 ml borate solution was added to each vial. B was placed at room temperature and 3 ml pNPG reagent added after 2 hours. The optical density of all three solutions were measured at 400 nm, and the activity calculated:

$$\text{Activity} = 2 * AGU_{st} * (H-B)/(HS-H)$$

where HS, H, and B are the OD of the solutions analysed, and $AGU_{st}$ is the activity of the AMG standard used.

Construction of pAMGY

The pAMGY vector was constructed as follows: The lipase gene in pJSO026 was replaced by the AMG gene, which was PCR amplified with the forward primer; FG2: 5'-CAT CCC CAG GAT CCT TAC TCA GCA ATG-3'and the reverse primer: RG2: 5'-CTC AAA CGA CTC ACC AGC CTC TAG AGT-3' using the template plasmid pLAC103 containing the AMG gene. The pJSO026 plasmid was digested with XbaI and SmaI at 37° C. for 2 hours and the PCR amplicon was blunt ended using the Klenow fragment and then digested with XbaI. The vector fragment and the PCR amplicon were ligated and transformed into E. coli by electrotransformation. The resulting vector is designated pAMGY.

The expression plasmid pJSO37 is described in WO 97/04079 and WO 97/07205. It is derived from pYES 2.0 by replacing the inducible GAL1-promoter of pYES 2.0 with the constitutively expressed TPI (triose phosphate isomerase)-promoter from Saccharomyces cerevisiae (Albert and Karwasaki, (1982), J. Mol. Appl Genet., 1, 419–434), and deleting a part of the URA3 promoter.

Construction of pLaC103

The A. niger AMGII cDNA clone (Boel et al., (1984), supra) is used as source for the construction of pLaC103 aimed at S. cerevisiae expression of the GII form of AMG.

The construction takes place in several steps, out lined below.

pT7-212 (EP37856/ U.S. Pat. No. 5,162,498) is cleaved with XbaI, blunt-ended with Klenow DNA polymerase and dNTP. After cleavage with EcoRI the resulting vector fragment is purified from an agarose gel-electrophoresis and ligated with the 2.05 kb EcoR1-EcoRV fragment of pBoel53, thereby recreating the XbaI site in the EcoRV end of the AMG encoding fragment in the resulting plasmid pG2x.

In order to remove DNA upstream of the AMG cds, and furnish the AMG encoding DNA with an appropriate restriction endonuclease recognition site, the following construct was made: The 930 bp EcoRI-PstI fragment of p53 was isolated and subjected to AluI cleavage, the resulting 771 bp Alu-PstI fragment was ligated into pBR322 with blunt-ended EcoRI site (see above) and cleaved with PstI In the resulting plasmid pBR-AMG', the EcoRI site was recreated just 34 bp from the initiation codon of the AMG cds.

From pBR-AMG' the 775 bp EcoRI-PstI fragment was isolated and joined with the 1151 bp PstI-XbaI fragment from pG2x in a ligation reaction including the XbaI-EcoRI vector fragment of pT7–212.

The resulting plasmid pT7GII was submitted to a BamHI cleavage in presence of alkaline phosphatase followed by partial SphI cleavage after inactivation of the phosphatase. From this reaction was the 2489 bp SphI-BamHI fragment, encompassing the S.c. TPI promoter linked to the AMGII cds.

The above fragment together with the 1052 bp BamHI fragment of pT7GII was ligated with the alkaline phosphatase treated vector fragment of pMT743 (EP37856/U.S. Pat. No. 5,162,498), resulting from SphI-BamHI digestion. The resulting plasmid is pLaC103.

Screening for Thermostable Glucoamylase Variants

The libraries are screened in the thermostable filter assay described below.

Filter Assay for Thermostability

Yeast libraries are plated on cellulose acetate filter(OE 67, Schleicher & Schuell, Dassel, Germany) on SC ura-agar plates with 100 $\mu$g/ml ampicillin at 30° C. for at least 72 hrs. The colonies are replica plated to nitrocellulose filters (Protran-Ba 85, Schleicher & Schuell, Dassel, Germany) and incubated at room temperature for 1 hours. Colonies are washed from Protran filters with tap water. Each filter is specifically marked with a needle before incubation in order to be able to localise positive variants on the filters after the screening. The Protran filters with bound variants are transferred to a container with 0.1 M NaAc, pH 4.5 and incubated at 55–75° C. for 15 minutes. The cellulose acetate filters on SC ura-agar plates are stored at room temperature until use. After incubation, the residual activities are detected on plates containing 5% maltose, 1% 50 mM NaAc, pH 4.5. The assay plates with Protran filters are marked the same way as the cellulose acetate filters and incubated for 2 hours at 50° C. After removal of the Protran filters, the assay plates are stained with Glucose GOD perid (Boehringer Mannheim GmbH, Germany). Variants with residual activity are detected on assay plates as dark green spots on white background. The improved variants are located on the storage plates. Improved variants are rescreened twice under the same conditions as the first screen.

General Method for Random Mutagenesis by use of the DOPE Program

Random mutagenesis may be carried out using the following steps:

1. Select regions of interest for modification in the parent enzyme,
2. Decide on mutation sites and non-mutated sites in the selected region,
3. Decide on which kind of mutations should be carried out, e.g., with respect to the desired stability and/or performance of the variant to be constructed,
4. Select structurally reasonable mutations, 5. Adjust the residues selected by step 3 with regard to step 4.
6. Analyze by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting glucoamylase variants by screening for the desired improved properties.

Dope Algorithm

Suitable dope algorithms for use in step 6 are well known in the art. One such algorithm is described by Tomandl, D. et al., 1997, Journal of Computer-Aided Molecular Design 11:29–38. Another algorithm is DOPE (Jensen, L J, Andersen, K V, Svendsen, A, and Kretzschmar, T (1998) Nucleic Acids Research 26:697–702).

EXAMPLES

Example 1

Construction of Glucoamylase Variants with N-terminal Extensions

Random Mutagenesis

The oligonucleotides AM11–18(with possibilities for inserting 1–7 extra amino acids after the KexII site and in front of the mature protein) and primer AM18 together with 2 primers corresponding to sequences about 75 bp outside the coding region in both the 5'(4244: 5'-TCA AGA ATA GTT CAA ACA AGA AGA-3') and 3' end (KB14: 5'-CTT TTC GGT TAG AGC GGA TG-3') are used to generate PCR-library-fragments by the overlap extension method (Horton et al., Gene, 77 (1989), pp. 61–68).

The following PCR reactions were performed:
PCR reaction 1: 4244 as 5' primer and AM18 as 3' primer.
PCR reaction 2: AM11 as 5' primer and KB14 as 3' primer (7 extra aa).
PCR reaction 3: AM12 as 5' primer and KB14 as 3' primer (6 extra aa).
PCR reaction 4: AM13 as 5' primer and KB14 as 3' primer (5 extra aa).
PCR reaction 5: AM14 as 5' primer and KB14 as 3' primer (4 extra aa).
PCR reaction 6: AM15 as 5' primer and KB14 as 3' primer (3 extra aa).
PCR reaction 7: AM16 as 5' primer and KB14 as 3' primer (2 extra aa).
PCR reaction 8: AM17 as 5' primer and KB14 as 3' primer (1 extra aa).
Template in the first reaction: pAMGY, template in reaction 2–8: either pAMGY or an improved variant cloned in the same vector. PCR reaction 9–15: The DNA from PCR reaction 1 together with either DNA from PCR reaction 2–8 were used as templates in the PCR reactions using 4244 as 5' primer and KB14 as 3' primer. These final PCR fragments were used in an in vivo recombination in yeast together with pJSOO26 cut with the restriction enzymes SmaI(or BamHI) and XbaI (to remove the coding region and at the same time create an overlap of about 75 bp in each end to make a recombination event possible).

AM11: 5'-GCA AAT GTG ATT TCC AAG CGC NNS NNS NNS NNS NNS NNS NNS GCG ACC TTG GAT TCA TGG TTG AGC-3' (SEQ ID NO: 2)

AM12: 5'-GCA AAT GTG ATT TCC AAG CGC NNS NNS NNS NNS NNS NNS GCG ACC TTG GAT TCA TGG TTG AGC-3' (SEQ ID NO: 3)

AM13: 5'-GCA AAT GTG ATT TCC AAG CGC NNS NNS NNS NNS NNS GCG ACC TTG GAT TCA TGG TTG AGC-3' (SEQ ID NO: 4)

AM14: 5'-GCA AAT GTG ATT TCC AAG CGC NNS NNS NNS NNS GCG ACC TTG GAT TCA TGG TTG AGC-3' (SEQ ID NO: 5)

AM15: 5'-GCA AAT GTG ATT TCC AAG CGC NNS NNS NNS GCG ACC TTG GAT TCA TGG TTG AGC-3' (SEQ ID NO: 6)

AM16: 5'-GCA AAT GTG ATT TCC AAG CGC NNS NNS GCG ACC TTG GAT TCA TGG TTG AGC-3' (SEQ ID NO: 7)

AM17: 5'-GCA AAT GTG ATT TCC AAG CGC NNS GCG ACC TTG GAT TCA TGG TTG AGC-3' (SEQ ID NO: 8)

AM18: 5'-GCG CTT GGA AAT CAC ATT TGC-3'(SEQ ID NO: 9)

4244: 5'-TCA AGA ATA GTT CAA ACA AGA AGA-3' (SEQ ID NO: 10)

KB14: 5'- CTT TTC GGT TAG AGC GGA TG-3' (SEQ ID NO: 11)

Example 2

Introduction of N-terminal Extension by Changing the KexII Recognition Site

A N-terminal extension can be introduced by removing or changing the KexII recognition site "KR" in front of the mature protein. An extension of 6 amino acids can then be introduced as the pro-sequence consist of 6 amino acids. In yeast KR is the optimal recognition site for Kex II. A change to RR will reduce the % of cleaved molecules (Bevan, A, Brenner, C and Fuller,R. s.1998, PNAS 95 (18): 10384–10389). Alternatively introduction of P in front of KR will reduce the % of cleaved molecules.

The pro-sequence was changed from NVISKR to either NVISRR or NVIPKR and gave approximately 50% AMG molecules with the extension NVISRR or NVIPKR and 50% normally processed mature AMG molecules.

Example 3

Construction of Glucoamylase (AMG 2) Variants Containing a Cysteine Bridge

The glucoamylase variant of the invention contains the following mutations: A479C or T480C or P481C or A471C or S431C or S8C or E299C or D375C and the peptide extension ACPPSTS and ASPPSTS. The parent glucoamylase (AMG 2) contains the following mutations: A479C or T480C or P481C or A471C or S431C or S8C or E299C or D375C.

The cysteine bridge was constructed as follows:
Site-directed Mutagenesis

For the construction of variants of the AMG G2 enzyme (SEQ ID NO: 11) the commercial kit, Chameleon double-stranded, site-directed mutagenesis kit was used according to the manufacturer's instructions.

The gene encoding the AMG G2 enzyme in question is located on pENI1542 prepared by cutting the plasmid pIVI9 with BamHI/XhoI (Cleaving out the coprinus peroxidase gene) and cloning in a AMG G2 containing pcr fragment (cut BglII/SalI), made by the use of the pLaC103 (containing the G2 cDNA) as template and the two primers 139123 (CGCACGAGATCTGCAATGTCGTTCCGATCTCTA) (SEQ ID NO: 12) and 139124

(CAGCCGGTCGACTCACAGTGACATACCAGAGCG) (SEQ ID NO: 13). This was confirmed by DNA sequencing, as was the variants. In accordance with the manufacturer's instructions the ScaI site of the Ampicillin gene of pNEI1542 was changed to a MluI site by use of the following primer:

7258: 5'p gaa tga ctt ggt tga cgc gtc acc agt cac 3' (SEQ ID NO: 14). (Thus changing the ScaI site found in the ampicillin resistance gene and used for cutting to a MluI site). The pENI1542 vector comprising the AMG gene in question was then used as a template for DNA polymerase and oligo 7258 (SEQ ID NO: 14) and 21401 (SEQ ID NO: 15). Primer no. 21401 (SEQ ID NO: 15) was used as the selection primer. 21401: 5'p gg gga tca tga tag gac tag cca tat taa tga agg gca tat acc acg cct tgg acc tgc gtt ata gcc 3' (SEQ ID NO: 15)

The introduction of a cysteine residue is introduced into the AMG gene in question by addition of an appropriate oligos comprising the desired mutation as follows:
Mutagenesis Oligo
ACPPSTS 137767 (SEQ ID NO: 16) (5'P-GTGATTTCCAGCGGTGCCCGCCGTC-CACGTCCGCGACCTTGGATTCATGG 3')
ASPPSTS 137766 (SEQ ID NO: 17) (5'P-GTGATTTCCAGCGGTCCCCGCCGTC-CACGTCCGCGACCTTGGATTCATGG 3')
D375C 137765(SEQ ID NO: 18) (5'P-GTAGCATTGTATGTGCCGTGAAGAC 3')
S431C 146826 (SEQ ID NO: 19) (5'P-ACCGTCGTAACTGCGTCGTGCCTGC 3')
E299C 146828 (SEQ ID NO: 20) (5'P-GTCTCAGTGACAGCTGCGCTGTTGCGGTG3')
A479C 146829 (SEQ ID NO: 21) (5'P-CCACTACGACGTGCACCCCCACTGG 3')
T480C 146830 (SEQ ID NO: 22) (5'P-CTACGACGGCTTGCCCCACTGGATCC 3')
P481C 146831 (SEQ ID NO: 23) (5'P-CGACGGCTACCTGCACTGGATCCGGC 3')
S8C 146827 (SEQ ID NO: 24) (5'P-TGGATTCATGGTTGTGTAACGAAGCGACC 3')

Mutants being made
ACPPSTS,D375C
ACPPSTS,S431C
ACPPSTS,E299C
ACPPSTS,A479C
ACPPSTS,T480C
ACPPSTS,P481C
ASPPSTS
S8C+A479C
S8C+T480C
S8C+P481C The mutations are verified by sequencing the whole gene. The plasmid was transformed into *A. oryzae* using the method described above in the "Materials and Methods" section. The variant was fermented and purified as described above in the "Materials and Methods" section.
Screening The library may be screened in the thermostability filter assays described in the "Material and Methods" section above.

Example 4
Glucoamylase Variants with Increased Thermal Stability

The thermal stability activity was measured at pH 4,5, 70° C. as described in Methods section above.

| Thermal stability at 70° C., pH 4.5 | | | |
|---|---|---|---|
| | Residual activity (%) | | |
| Enzyme | 5 min | 20 min | 40 min |
| AMG, G2 (wt) | 71 | 21 | 2 |
| NVIPKR | 85 | 31 | 8 |
| PLALSD | 73 | 26 | 8 |

The result shows that it is possible to increase the thermal stability by linking an extension at the N-terminal of a glucoamylase enzyme according to the invention.

Example 5

Glucoamylase Variants with Increased Thermal Stability

The thermal stability activity of improved variants expressed in yeast was measured on crude samples at pH 4.5, 68° C., as described in Methods section above.

| Thermal stability at 68° C., pH 4.5 | | | |
|---|---|---|---|
| | Residual activity (%) | | |
| Enzyme | 5 min | 10 min | 20 min |
| AMG, G2 (wt) | 57 | 29 | 16 |
| ISN | 65 | 39 | 28 |
| MN | 65 | 39 | 28 |
| MPGRLP | 56 | 34 | 23 |
| IFELTPR | 55 | 38 | 22 |
| LGPD | 62 | 28 | 23 |
| LGVTGE | 55 | 32 | 22 |
| AGPLTPR | 50 | 33 | 22 |
| PCSAGE | 57 | 26 | 21 |
| PLASD | 67 | 47 | 36 |
| NVIPKR | 57 | 35 | 23 |

Example 6

Glucoamylase Variants with Increased Thermal Stability

The thermal stability activity of improved variants expressed in *A. niger* was measured on crude samples at pH 4,5, 70° C. as described in Methods section above.

| Variant | Residual activity (%) 40 min |
|---|---|
| G2 | 4 |
| ACPPSTS + E299C | 19 |
| ACPPSTS + A479C | 11 |
| ACPPSTS + T480C | 24 |

N-terminal analysis of the variant ACPPSTS+E299C showed that no free cysteine or oxidized cysteine were present in the N-terminal of this variant indicating that an —SS— bond had been formed between the Cysteine in the N-terminal and Cysteine in position 299.

What is claimed is:

1. A variant glucoamylase having an amino acid sequence that differs from the amino acid sequence of a parent glucoamylase, wherein the difference between the amino acid sequence of the variant glucoamylase and the amino acid sequence of the parent glucoamylase comprises a peptide extension linked to the N-terminal amino acid residue and wherein the peptide extension is:
   Asn-Val-Ile-Ser-Arg-Arg (SEQ ID NO:36), or
   Asn-Val-Ile-Pro-Lys-Arg (SEQ ID NO:37), or
   Ala-Ser-Pro-Pro-Ser-Thr-Ser (SEQ ID NO:38), or
   Pro-Leu-Ala-Leu-Ser-Asp (SEQ ID NO:41), or
   Leu-Gly-Val-Thr-Gly-Glu (SEQ ID NO:42), or Ala-Gly-Pro-Leu-Pro-Ser-Glu (SEQ ID NO:43), or
Leu-Gly-Pro-Asp (SEQ ID NO:44), or
Ile-Phe-Glu-Leu-Thr-Pro-Arg (SEQ ID NO:45), or
Ile-Ser-Asn, or
Met-Asn, or
a peptide of formula (I):

$$\text{Xaa-C-(Xaa)}_n \tag{I},$$

wherein each Xaa is independently an amino acid.

2. The variant glucoamylase of claim 1, wherein the peptide extension is Asn-Val-Ile-Ser-Arg-Arg (SEQ ID NO:36).

3. The variant glucoamylase of claim 1, wherein the peptide extension is Asn-Val-Ile-Pro-Lys-Arg (SEQ ID NO:37).

4. The variant glucoamylase of claim 1, wherein the peptide extension is Ala-Ser-Pro-Pro-Ser-Thr-Ser (SEQ ID NO:38).

5. The variant glucoamylase of claim 1, wherein the peptide extension is Pro-Leu-Ala-Leu-Ser-Asp (SEQ ID NO:41).

6. The variant glucoamylase of claim 1, wherein the peptide extension is Leu-Gly-Val-Thr-Gly-Glu (SEQ ID NO:42).

7. The variant glucoamylase of claim 1, wherein the peptide extension is Ala-Gly-Pro-Leu-Pro-Ser-Glu (SEQ ID NO:43).

8. The variant glucoamylase of claim 1, wherein the peptide extension is Leu-Gly-Pro-Asp (SEQ ID NO:44).

9. The variant glucoamylase of claim 1, wherein the peptide extension is Ile-Phe-Glu-Leu-Thr-Pro-Arg (SEQ ID NO:45).

10. The variant glucoamylase of claim 1, wherein the peptide extension is Ile-Ser-Asn.

11. The variant glucoamylase of claim 1, wherein the peptide extension is Met-Asn.

12. The variant glucoamylase of claim 1, wherein the peptide extension is a peptide of formula (I):

$$\text{Xaa-Cys-(Xaa)}_n \tag{I},$$

wherein each Xaa is independently an amino acid.

13. The variant glucoamylase of claim 12, wherein each Xaa is independently a non-α-helix maker.

14. The variant glucoamylase of claim 13, wherein the non-α-helix maker is selected from the group consisting of M, K, H, V, I, Y, C, F, T, G, N, P, S and D.

15. The variant glucoamylase of claim 12, wherein peptide extension consists of 3–100 amino acid residues.

16. The variant glucoamylase of claim 15, wherein the peptide extension consists of 3–50 amino acid residues.

17. The variant glucoamylase of claim 16, wherein the peptide extension consists of 3–20 amino acid residues.

18. The variant glucoamylase of claim 17, wherein the peptide extension consists of 3–10 amino acid residues.

19. The variant glucoamylase of claim 12, wherein the peptide extension is a peptide of formula (II):

$$\text{Xaa-Cys-Xaa-Xaa-Xaa-Xaa-Xaa,}$$

wherein each Xaa independently is selected from the group consisting of M, K, H, V, I, Y, C, F, T, G, N, P, S and D.

20. The variant glucoamylase of claim 12, wherein the peptide extension is:
   Ala-Cys-Gly-Pro-Ser-Thr-Ser (SEQ ID NO: 25),
   Ala-Cys-Pro-Gly-Thr-Ser-Thr (SEQ ID NO: 26),
   Ala-Cys-Gly-Thr-Gly-Thr-Ser (SEQ ID NO: 27),
   Ala-Cys-Thr-Gly-Ser-Thr-Gly (SEQ ID NO: 28),
   Ala-Cys-Gly-Pro-Ser-Thr-Ser-Gly (SEQ ID NO: 29),
   Ala-Cys-Pro-Gly-Thr-Ser-Thr-Gly (SEQ ID NO: 30),
   Ala-Cys-Gly-Thr-Gly-Thr-Ser-Ser (SEQ ID NO: 31),
   Ala-Cys-T-Gly-Ser-Thr-Gly-Thr (SEQ ID NO: 32),
   Ala-Cys-Pro-Pro-Ser-Thr-Ser (SEQ ID NO:39), or
   Pro-Cys-Ser-Ala-Gly-Glu (SEQ ID NO:40).

21. The variant glucoamylase of claim 12, wherein a cysteine residue of the peptide extension forms a cysteine bridge with a cysteine residue of the parent glucoamylase.

22. The variant glucoamylase of claim 1, wherein the parent glucoamylase is a microbial glucoamylase.

23. The variant glucoamylase of claim 22, wherein the parent glucoamylase is a filamentous fungal glucoamylase.

24. The variant glucoamylase of claim 23, wherein the parent glucoamylase is an *Aspergillus niger* glucoamylase.

25. The variant glucoamylase of claim 24, wherein the parent glucoamylase is the *Aspergillus niger* G1 or G2 glucoamylase.

26. The variant glucoamylase of claim 12, wherein the parent glucoamylase comprises an insertion of a cysteine residue or a substitution of an amino acid residue with a cysteine residue.

27. The variant glucoamylase of claim 26, wherein the parent glucoamylase is *Aspergillus niger* G1 glucoamylase (SEQ ID NO:1) comprising
   (a) a substitution of serine at position 8 with cysteine;
   (b) a substitution of glutamic acid at position 299 with cysteine;
   (c) a substitution of aspartic acid at position 375 with cysteine;
   (d) a substitution of serine at position 431 with cysteine;
   (e) a substitution of alanine at position 471 with cysteine;
   (f) a substitution of alanine at position 479 with cysteine;
   (g) a substitution of threonine at position 480 with cysteine; and/or
   (h) a substitution of proline at position 481 with cysteine.

28. The variant glucoamylase of claim 1, wherein the variant has improved thermal stability compared to the parent glucoamylase.

* * * * *